(12) United States Patent
Hightower (10) Patent No.: US 8,617,240 B2
(45) Date of Patent: Dec. 31, 2013

(54) MOLDABLE CUSHION FOR IMPLANTS

(76) Inventor: Charles D. Hightower, Minneapolis, MN (US)

( * ) Notice: Subject to any disclaimer, the term of this patent is extended or adjusted under 35 U.S.C. 154(b) by 366 days.

(21) Appl. No.: 12/948,448

(22) Filed: Nov. 17, 2010

(65) Prior Publication Data
US 2012/0123539 A1  May 17, 2012

(51) Int. Cl.
*A61F 2/02* (2006.01)
(52) U.S. Cl.
USPC ............ 623/11.11; 623/23.58; 623/23.72
(58) Field of Classification Search
USPC ........... 623/11.11, 14.12, 21.58, 23.71, 23.72
See application file for complete search history.

(56) References Cited

U.S. PATENT DOCUMENTS

| | | | | |
|---|---|---|---|---|
| 3,829,904 A * | 8/1974 | Ling et al. | .................. | 623/22.39 |
| 5,556,429 A | 9/1996 | Felt | | |
| 5,641,502 A | 6/1997 | Skalla et al. | | |
| 5,658,582 A | 8/1997 | Dorigatti et al. | | |
| 5,702,456 A | 12/1997 | Pienkowski | | |
| 5,888,223 A * | 3/1999 | Bray, Jr. | ..................... | 623/17.16 |
| 6,423,332 B1 | 7/2002 | Huxel et al. | | |
| 6,530,956 B1 | 3/2003 | Mansmann | | |
| 6,756,060 B1 | 6/2004 | Greenspan et al. | | |
| 6,911,212 B2 | 6/2005 | Gertzman et al. | | |
| 7,105,018 B1 | 9/2006 | Yip et al. | | |
| 7,201,917 B2 | 4/2007 | Malaviya et al. | | |
| 7,361,195 B2 | 4/2008 | Schwartz et al. | | |
| 8,206,447 B2 * | 6/2012 | De Villiers et al. | ........ | 623/17.14 |
| 2001/0000352 A1 | 4/2001 | Hayes | | |
| 2002/0143384 A1 | 10/2002 | Ozasa | | |
| 2003/0036797 A1 | 2/2003 | Malaviya et al. | | |
| 2003/0097182 A1 | 5/2003 | Buchman et al. | | |
| 2004/0030402 A1 | 2/2004 | Arnin et al. | | |
| 2004/0062816 A1 | 4/2004 | Atkinson et al. | | |
| 2004/0133275 A1 | 7/2004 | Mansmann | | |
| 2004/0143344 A1 | 7/2004 | Malaviya et al. | | |
| 2004/0167637 A1 * | 8/2004 | Biscup | ........................ | 623/23.75 |
| 2004/0192643 A1 | 9/2004 | Pressato et al. | | |
| 2004/0230315 A1 * | 11/2004 | Ek | ............... | 623/23.51 |
| 2004/0250729 A1 | 12/2004 | Jang et al. | | |
| 2005/0043808 A1 * | 2/2005 | Felt et al. | .................... | 623/20.14 |
| 2005/0049596 A1 * | 3/2005 | Stewart | ........................... | 606/72 |
| 2005/0287187 A1 | 12/2005 | Mansmann | | |
| 2006/0041320 A1 | 2/2006 | Matsuda | | |
| 2006/0057182 A1 | 3/2006 | Oliver et al. | | |
| 2006/0135912 A1 | 6/2006 | Chernomorsky et al. | | |
| 2006/0165962 A1 | 7/2006 | Borck et al. | | |
| 2007/0016302 A1 * | 1/2007 | Dickman | .................... | 623/17.13 |
| 2007/0020314 A1 | 1/2007 | Haro et al. | | |
| 2007/0191851 A1 | 8/2007 | Ashammakhi | | |
| 2007/0275032 A1 | 11/2007 | Wimmer et al. | | |
| 2008/0154368 A1 * | 6/2008 | Justis et al. | ................. | 623/11.11 |
| 2008/0234790 A1 | 9/2008 | Bayer et al. | | |
| 2008/0294193 A1 * | 11/2008 | Schwartz et al. | ............. | 606/228 |
| 2009/0246244 A1 | 10/2009 | McKay et al. | | |
| 2010/0303911 A1 * | 12/2010 | Sheardown et al. | .......... | 424/486 |

* cited by examiner

*Primary Examiner* — David Isabella
*Assistant Examiner* — Randy Shay
(74) *Attorney, Agent, or Firm* — Thomas J. Nikolai; Nikolai & Mersereau, P.A.

(57) ABSTRACT

Custom moldable cushions for covering medical implants fastened to a bone are provided. Such cushions inhibit irritation of the surrounding soft tissue by covering the bone-implant interface and by reducing friction caused by movement of soft tissue adjacent the implant. Such cushions may also be employed to spread and absorb forces reducing patient discomfort and risk of injury and infection associated with such implants.

21 Claims, 6 Drawing Sheets

MOLDABLE CUSHION FOR IMPLANTS

CROSS-REFERENCED TO RELATED APPLICATIONS

Not applicable.

STATEMENT REGARDING FEDERALLY SPONSORED RESEARCH OR DEVELOPMENT

Not applicable.

BACKGROUND OF THE INVENTION

I. Field of the Invention

The present invention relates to implanted orthopedic, maxillofacial, spinal and plastic surgery hardware. More specifically, the present invention relates to cushions which cover such hardware to cushion the surrounding tissue from such hardware.

II. Related Art

Orthopedic implants made of various materials are employed to provide adequate strength to resist biologic stress across a pathologic area during bone healing. Orthopedic implants are often made of metal such as titanium which can be forged or bent in a variety of ways to allow such implants to conform to a surface of the bone to some degree while maintaining the mechanical properties of the implant. Despite new advances in low profile implant technologies, metal implants are limited in their ability to match the contour of the underlying bone. The result is often a step-off at the bone-implant interface. The existence of such a step-off can cause a variety of issues. Such a step-off is often the site of discomfort for patients, particularly when skin, muscle, or other tissues are pushed against the step-off. In addition, the surfaces of metal implants are a source of friction between such implants and surrounding soft tissues which are constantly moving. Problems arising from such friction are most extreme when a tendon is overlying the implant. Such friction can not only cause painful tendonitis, but can also eventually lead to a rupture of the tendon.

Screws are sometimes used alone or to fasten plates, rods, and other orthopedic implants. Whether used alone or to fasten another orthopedic implant in place, the screws are often prominent and painful. For example, in spinal fusion surgery screws are typically placed low in the back where soft tissue coverage is thin and pressures from the waist line of clothing and belts or furniture when sitting is significant. The result is often painful irritation. In extreme cases, the implanted hardware can erode through the skin causing dangerous ulceration requiring prolonged wound care and increased risk of infection. All too often secondary surgeries are required to remove the hardware, reposition the hardware or graft skin to treat such an ulcer.

Issues of the type described above are not uniquely associated with orthopedic implants. Dental and maxillofacial implants used to treat or repair bones of the jaw and face and similar implants used in plastic surgery often result in a step-off at the bone-implant interface or in friction between the implant and soft tissue covering the implant. Such a step-off or friction can lead to substantial discomfort and in severe cases ulceration, infection, and damage to the surrounding tissue.

Various attempts have been made to address step-offs at the bone-implant interface of plates used to treat bone fractures. Most involve efforts to alter the contours of the implant to reduce the step-off. Pre-formed plastic covers with tapered edges have also been employed to cover such plates. Neither of these two approaches have successfully or universally solved the significant problems which exist. The significant limitations of these two approaches becomes apparent after a surgeon modifies the plate shape to fit the affected bone. Bones have significant individual differences in shape. Failing to properly modify the shape of the plate to fit the bone can cause poor fracture healing if the bone fragments are not properly opposed. When the surgeon modifies the shape of the hardware to provide proper opposition of the bone fragments, the prominence of the hardware and the bone-implant step-off often becomes exaggerated. Also, once the shape of the plate has been modified, preformed plastic covers often no longer fit the implant. The application of a preformed plastic cover after the surgeon modifies the shape of the plate so the bone fragments are properly opposed is often not possible or the result is an unacceptably loose, insecure fit between the plate and the cover. For such a cover to be used and provide any benefit it must not only be securely locked to the plate so it does not float within the body, but it must also reduce the bone-implant step-off. While such covers can be designed to fit a plate of a particular shape and reduce the step-off, any change in the shape of the plate can result in the cover exacerbating rather than reducing this step-off.

Various malleable polymers have been employed to fill bone voids and as bone graft alternatives. The use of such materials has broad application in the field of dentistry to fill voids in teeth. Such materials have also been used to act as a scaffolding for bone healing. These materials have different properties to allow for varying work times, stiffness, and strength. For a variety of reasons, such materials have rarely, if ever, been used to reduce friction between an implant and surrounding tissue or a step-off at the bone-implant interface.

Other bio-absorbable polymers have been employed in the design of internal bandages to allow for guided tissue regeneration or to prevent adhesion of tissue at a surgical site during healing. These materials have not been employed to either reduce friction or to reduce a bone-implant step-off. The use of a bio-absorbable material would likely only temporarily reduce friction. Also, generation of tissue around an implant could make explantation more difficult and give rise to a number of other anatomical issues making the use of such materials undesirable.

In view of the foregoing, there continues to exist a real, significant and long-felt need for an apparatus which successfully and nearly universally addresses the problems associated with a bone-implant step-off and at the same time reduces friction between the implant and surrounding tissue.

SUMMARY OF THE INVENTION

The present invention provides various medical implant cushions comprising a bio-compatible, non-absorbable polymer having a first state and a second state. When the polymer is in its first state, the polymer is malleable in vivo so it can be formed into a desired shape to easily and securely seat the cushion onto the implant and provide a cushioning layer between an implant and the surrounding tissue which may otherwise be irritated by the contours of the implant. When the polymer is in its second state, the polymer retains its desired shape. The polymeric material of such an implant cushion can be shaped by the surgeon to cover any bone-implant step-off and provide a smooth, custom taper between the cover and the bone. In this way, a cushion made in accordance with the present invention minimized discomfort and the risk of irritation, injury, or infection caused by a prominent bone-implant step-off.

The polymeric material(s) used in the construction of such an implant cushion can be lubricious or impregnated with a lubricant to reduce friction between the surfaces of the implant and surrounding tissue thereby reducing the risk that such tissue (such as a tendon or other soft tissue) will rupture or become irritated or ulcerated. The polymeric material used in constructing the cushion, when the polymer is in its second polymerization state, is also preferably mildly visco-elastic. As such, there is a more natural transition between the implant and surrounding natural tissue when felt through the skin from above and the cushion will absorb contact stress by deforming under applied pressure and then regaining its shape as the pressure is removed.

Sometimes it will be desirable to remove the implant. Removal of the implant may be required to address infection, hardware breakage, or a subsequent injury adjacent the implant site. Thus, the implant cushion should be easily removable from the implant. Likewise, a radio-opaque strip or other identification codes can be included in the cushion to enhance patient safety and to enable accounting for the cushion during routine radiographic follow-up via X-ray or the like.

DETAILED DESCRIPTION OF THE INVENTION

Figure 1:
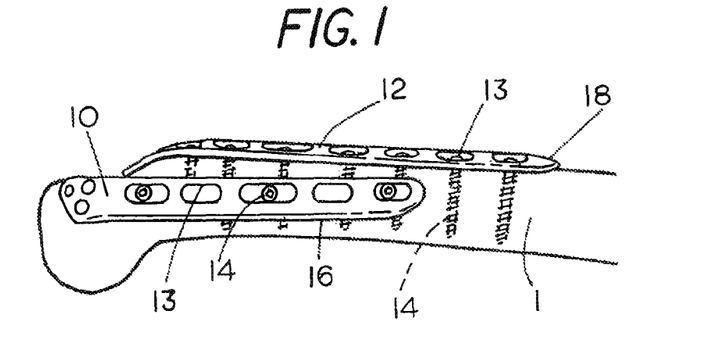
FIG. 1 is a perspective view showing two orthopedic implant plates used to repair a bone fracture.

FIGS. 1-5 show representative examples of the types of implants employed by surgeons today. FIG. 1 shows a bone 1 which has been fractured and a pair of orthopedic implant plates 10 and 12 employed for fixation of the fracture. Each plate has a plurality of holes 13 surrounded by a recessed flange. The plates are made of a suitable metal such as titanium. Screws 14 are used to fasten the plates 10 and 12 to the bone 1. The screws 14 include a threaded shaft having a diameter smaller than the hole 13 and a head which engages the recessed flange surrounding the hole 13 to fix the plate 10 or 12 to the bone 1. The bone-implant step-off associated with plate 10 is shown at 16. The bone-implant step-off associated with plate 12 is shown at 18. As shown, the shape of each of plates 10 and 12 has been modified to match the contours of the bone 1 and provide a proper alignment between the bone fragments on opposite sides of the fracture.

Figure 2:
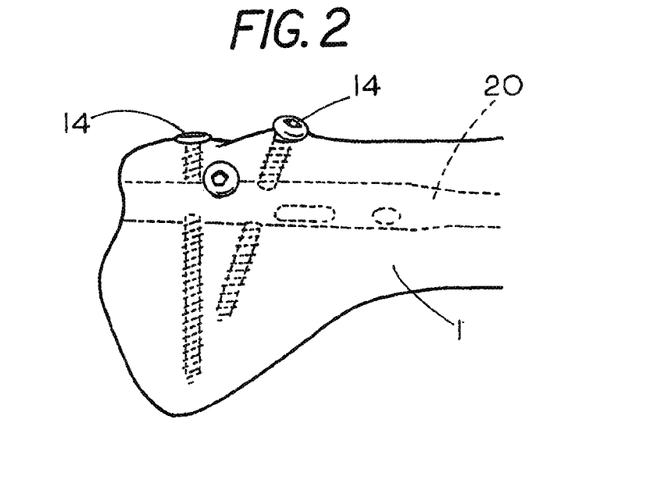
FIG. 2 is a perspective view showing an intramedullary nail device implanted in a bone with plurality of interlocking screws.

FIG. 2 shows a rod 20 which has been placed within bone 1 to stabilize the bone. A plurality of screws 14 are used to secure the rod 20 in place. The screws pass through the bone 1 and the rod 20 at a variety of angles. The head of each screw 14, and in some cases a portion of the threaded shaft of a screw 14, projects from the surface of the bone providing a bone-implant step-off and an unnatural exposed surface.

Figure 3:
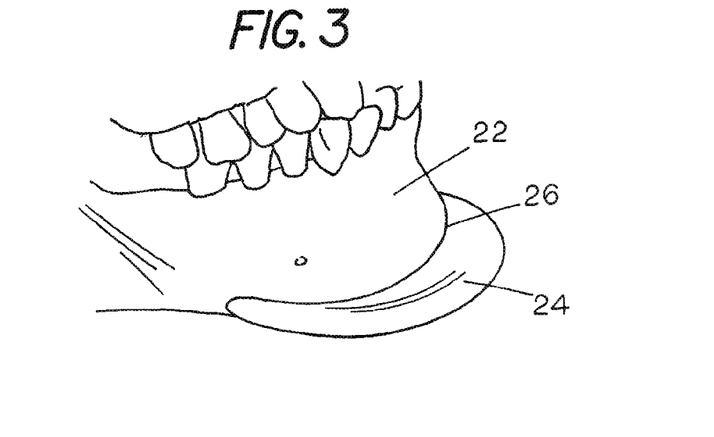
FIG. 3 is a perspective view of an augmentation implant being employed to augment the bone structure of a chin.

FIG. 3 shows a chin implant 24 attached to the bone of the chin 22 by a suitable adhesive. The chin implant 24 can be made of a suitable metal such as titanium or a medical grade plastic. As shown, there is a considerable step-off 26 at the bone-implant interface.

Figure 4:
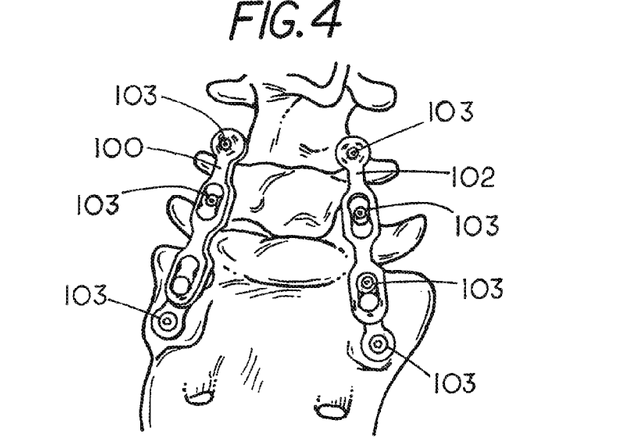
FIG. 4 is a perspective view of a first type of spinal fusion hardware.
Figure 5:
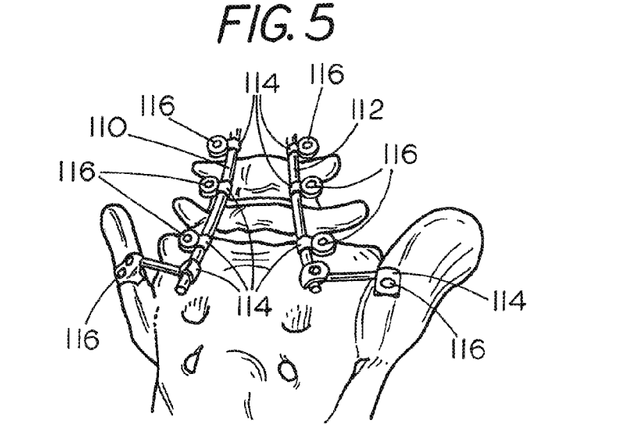
FIG. 5 is a perspective view of a second type of spinal fusion hardware.

FIGS. 4 and 5 show two styles of implants used in performing a spinal fusion. The implant shown in FIG. 4 comprises two sets of plates 100 and 102 attached to bone using pedicle screws 103. The implant shown in FIG. 5 comprises a pair of rods 110 and 112. Each rod is secured to bone using hooks 114 and pedicle screws 116. Implants of the type shown in FIGS. 4 and 5 are often positioned at the lower aspect of the spine near the patient's waist. This area of the body is typically subjected to a number of external forces such as by the waste band of clothing or furniture when sitting. Such forces cause the a soft tissue surrounding the implant to constantly rub across the surfaces and edges of the implant. Irritation, infection and ulceration of the surrounding tissue can result.

Figure 6:
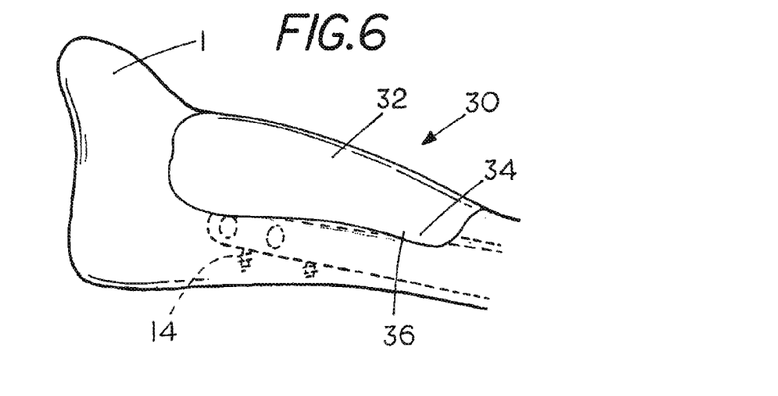
FIG. 6 is a perspective view of an implant cushion covering an orthopedic implant plate and an adjacent portion of the bone to which the implant plate has been attached.

FIG. 6 shows a first embodiment of a cushion 30 being employed to cover an orthopedic implant plate such as 10 or 12 in FIG. 1. The implant cushion 30 shown in FIG. 3 has a main body 32 covering the implant (not visible) and the heads of the screws 14. The implant cushion 30 also has an edge portion 34 which covers the step-off of the bone-implant interface and is feathered into the bone 1 to virtually eliminate any step-off at the cushion-bone interface 36.

The cushion 30 shown in FIG. 1 is preferably made of a biocompatible polymer which is not absorbable by the human body. The polymer has a first state in which the polymer is malleable within the body (in vivo) so it can be formed into a desired shape such as that shown in FIG. 6. The polymer also has a second polymerization state in which the cushion retains its desired shape. Cushion 30 is shaped to provide a cushioning layer between the implant and the surrounding tissue which may otherwise be irritated by the contours of the implant.

How the polymer used to construct cushion 30 transitions from its first state to its second state will depend on the polymer employed. Some polymers will make this state change at body temperature or when exposed to body fluids. Others will change from the first to the second state when exposed to light of predetermined wavelengths. The polymer employed to construct cushion 30 should either be lubricious or impregnated with a biocompatible lubricant. Suitable lubricants include, but are not limited to, lubricin and hyaluronic acid. When in its second state, the polymer selected should be somewhat visco-elastic. Using a visco-elastic material minimizes palpable differences between an implant covered with the cushion 30 and the native soft tissue adjacent to the implant when felt through the overlying skin. The use of a visco-elastic material will also absorb some of the shock when an external force is applied to the implant site thus offering some protection not only to the implant covered by cushion 30, but also to the surrounding tissue.

Various polymers can be employed in forming the cushion 30 and the invention is not limited to any particular polymer. The polymer could be any of a number of foam, hydrogel or malleable solid plastic materials. The polymer could also consist of a hydrolytic and oxidative stable thermoplastic polyurethane like a poly (dimethyl siloxane) derivative, or a cross-linked hyaluronan of adequate durability.

To permit removal of the cushion 30 from the implant, the implant can be formed with one or more scored channels on the under surface of the cushion 30 and corresponding markings identifiable on the outer surface which allow the cushion 30 to be split for removal. For alignment, location, or identification purposes, a radio-opaque material may be embedded in the implant cushion 30.

Figure 7:
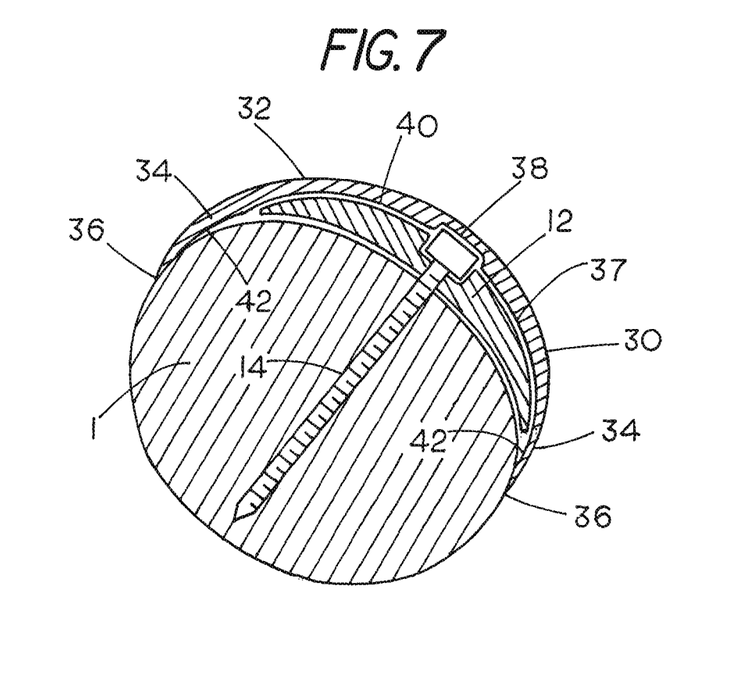
FIG. 7 is a cross-sectional view showing an implant attached to a bone using a screw and covered by an implant cushion.

FIGS. 6 and 7 are provided to illustrate the cushion 30 being employed in conjunction with an implant plate 12 which has been attached to a bone 1 with screws 14. As shown, the cushion 30 has a first portion 32 covering the plate 12, a second portion 34 covering adjacent portions of the bone 1, and a cushion-bone interface 36 providing a smooth, feathered transition between the bone 1 and the cushion 30.

FIG. 7 shows the molded negative under surface 37 of the cushion 30. As shown, the molded negative under surface 37 has a contour 38 matching the contours of the head of the screw 14 used to attach the plate 12 to the bone 1. The molded negative under surface 37 also has a main body portion 40 matching the shape of the plate 12, and contours 42 matching the shape of the adjacent portions of bone 1. These contours assist in securing the cushion 30 to the implant.

Figure 8:
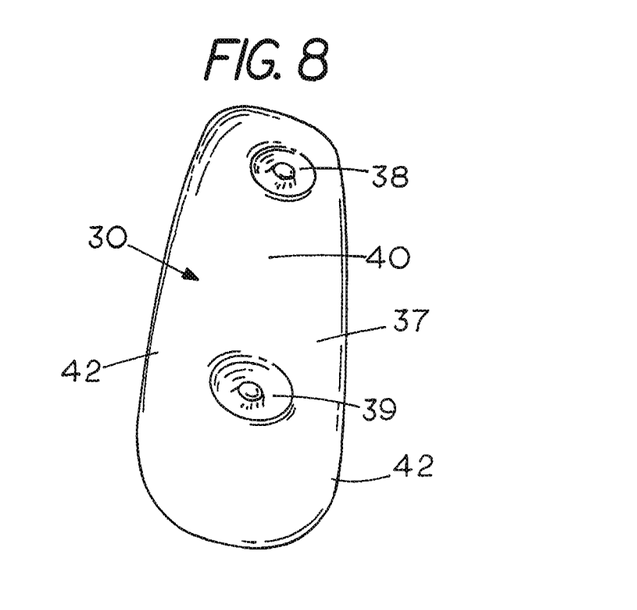
FIG. 8 is a perspective view showing the negative inner surface of the implant cushion of FIG. 7.

While FIGS. 6-7 illustrate how the cushion 30 forms a protective layer over an implant comprising a plate 12 and screws 14, the implant can take other forms and the cushion 30 can be molded in a similar fashion to such implants. For example, the implant can simply comprise screws such as 14 or an implant such as the implant shown in FIG. 2. In such cases, the molded negative under surface of 37 may be as shown in FIG. 8. As illustrated in FIG. 8, the molded inner surface 37 has contours 38 and 39 matching the contours of the heads of two screws, a main body portion 40 covering the area of bone separating the screw heads and an edge portion 42 forming a smooth, feathered transition between the cushion 30 and the bone. The cushion 30 forms a protective (e.g., lubricious) layer not only over the implant, but also over an edge of the implant and the adjacent exposed portion of the bone, irrespective of the type of implant, to reduce any trauma associated with the bone-implant interface. Likewise, the implant can be any augmentation implant. One example of an augmentation implant is the implant 24 shown in FIG. 3. When used with an augmentation implant, the contours of the cushion will be dictated by the shape of the implant 24, the adjacent portions of bone 22, the bone-implant interface 26, and often cosmetic considerations.

From the foregoing, those skilled in the art will appreciate the thickness of the cushion 30 will not be uniform. The surgeon can mold the implant cushion over the implant after the implant has been installed as the needs of the patient dictate. The implant will tend to be thinner across flat surfaces with no changes in elevation and tend to be thicker in areas where the contours of the implant or bone-implant interface present elevational changes. In some cases, the surgeon may elect to thicken the cushion for cosmetic purposes or to provide extra cushioning in areas subjected to substantial external pressure. By way of example, spinal fusion surgery implants such as those shown in FIGS. 4 and 5 typically include at least one plate rod screwed in place near the base of the spine. In this area, the surgeon may elect to increase the thickness of the cushion to absorb and spread over a larger area outside forces associated with sitting.

Figure 9:
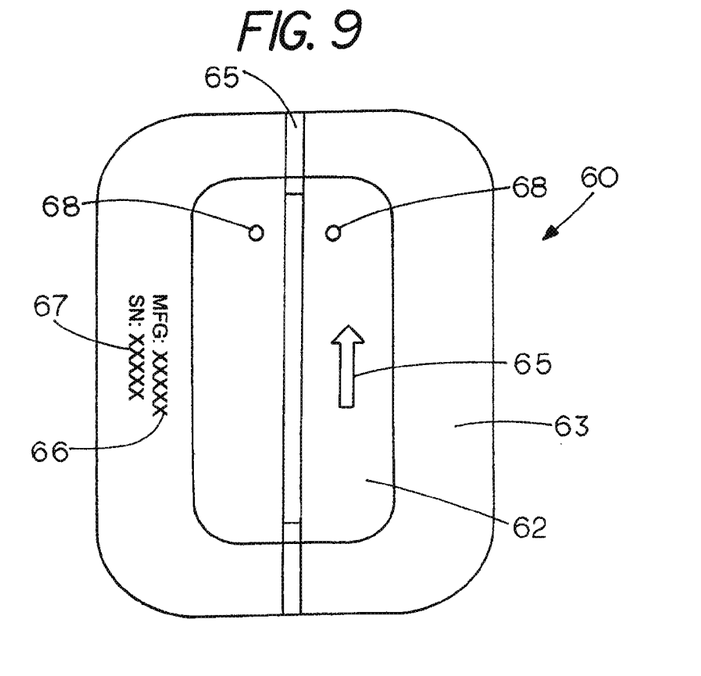
FIG. 9 is a top plan view of another implant cushion.
Figure 10:
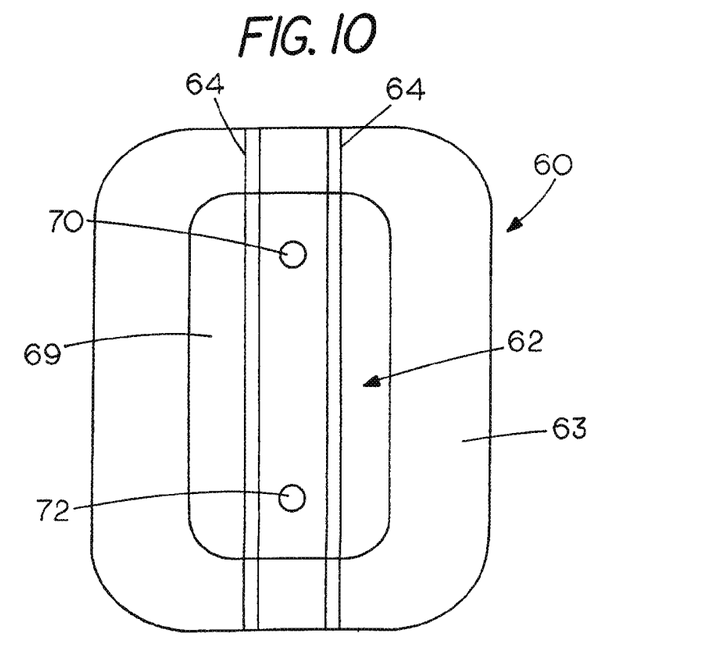
FIG. 10 is a bottom plan view of the implant cushion shown in FIG. 9.
Figure 11:
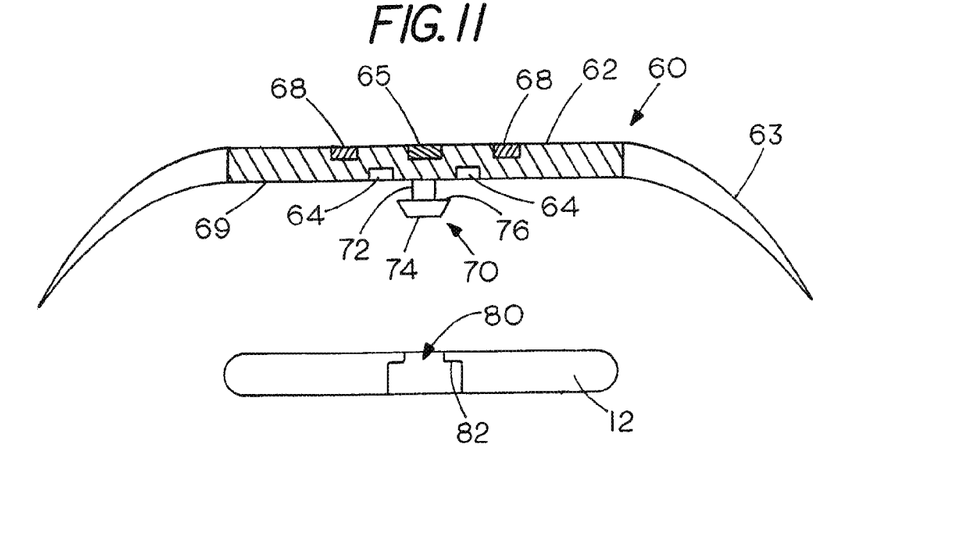
FIG. 11 is an exploded cross-sectional view showing an implant and an implant cushion.

FIGS. 9-11 illustrate an alternative embodiment of a cushion 60 made in accordance with the present invention. Cushion 60 is ideally suited for application to an orthopedic implant such as plate 12. The cushion 60 has a center portion 62. Surrounding the center portion 62 is an edge portion 63. The center portion 62 and the edge portion 63 can be constructed of the same material or different materials. The center portion 62 and the edge portion 63 each should be made of a bio-compatible, non-absorbable polymer. The polymer used to form the edge portion 63 should have a first state in which the polymer is malleable in vivo so it can be formed into a desired shape and a second state in which the polymer retains its desired shape. When the center portion 62 is constructed of the same material as the edge portion 63, the material of the center portion 62 (but not the material of the edge portion 63) is converted to the second state during manufacture or otherwise prior to implantation. The material of the edge portion 63 is preferably not converted to the second state until after the surgeon has had the opportunity to mold the outer portion over the bone-implant interface and adjacent portions of the bone.

As shown in FIG. 9, the top of the cushion 60 is marked with an indexing indicia 65 and with identification indicia 66 and 67. The identification indicia can include, for example, the name of the manufacturer 66 and a serial number 67. The identification indicia 66 and 67 are preferably printed using an indelible radio-transparent material so as to not interfere with X-ray evaluation of the bone and soft tissue. The indexing indicia 65 should be radio-opaque. This permits orientation of the cushion to be ascertained via an X-ray after implantation. The indexing indicia 65 should be in the form of a thin strip extending along the length of the cushion 60 so the indicia 65 may be detected without unduly inhibiting X-ray evaluation of the bone and soft tissue. The top of cushion 60 also has a pair of orifices 68 which are engaged by a surgical tool (see FIG. 16) to grip the cushion and then position the cushion 60 in vivo over the plate 12 to which the cushion 60 is then attached.

FIG. 10 shows the bottom of the cushion. Again, the center portion 62 and the edge portion 63 are shown. The edge portion 63 is made of a biocompatible, non-absorbable polymer left in its first state until after the cushion 60 has been secured to the plate 12 and the surgeon has molded the edge portion 63 into the desired shape. The edge portion 63 then transforms into its second state by, for example, further polymerization of the material due to temperature, light or some other means. Projecting from the negative under surface 69 of the center portion 62 is a pair of button tabs 70 and 72. These are used to assist in providing a secure connection between the cushion 60 and the implant plate 12. While two such button tabs 70 and 72 are shown, those skilled in the art will recognize the advantages associated with using only one such button tab (e.g., when the shape of the plate 12 has changed substantially during implantation) or more than two button tabs (e.g., to provide a more secure fixation of the cushion to the plate or when a single cushion 60 is to be secured to a plurality of plates). The bottom of cushion 60 also includes one or more scorings or channels 64. Two such channels are shown in FIG. 10. These channels assist with removal of the cushion 60 in the event removal becomes necessary.

Figure 12:
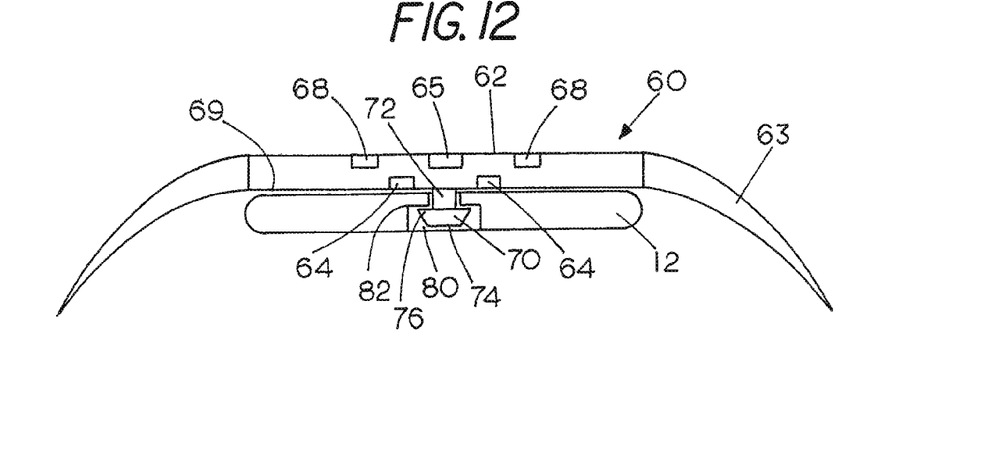
FIG. 12 is a cross-sectional view showing the implant and implant cushion of FIG. 11.

FIGS. 11 and 12 show not only the cushion 60, but also the plate 12. As shown, the button tab 70 has a shaft 72 extending from the bottom of the center section 62 of the cushion 60.

The button tab 70 also has a projection 74 extending outwardly from the shaft to provide a flange 76. To attach the cushion 60 to the plate 12 after the plate 12 has been fastened to a bone, the surgeon uses an elongate surgical tool (not shown) which grips the center section 60 using the orifices 68 and aligns the cushion 60 so that the button tab 70 is positioned adjacent the hole 80 in the plate 12. A force is then applied to the cushion 60 to move the projection 74 of button tab 70 through hole 80 so that the flange 76 of the projection 74 engages the flange 82 of hole 80 to lock the cushion 60 to the plate 12. This can be done using the surgical tool or by manually applying pressure to the cushion 60. With the surgical tool removed and the button tab 70 inserted into hole 80, the surgeon molds the edge portion 63 into the desired shape. Finally, the edge portion 63 is converted from its first state to its second state to fix the shape of the edge portion 63 and further secure the cushion 60 to the implant plate 12. Causing the material of the edge portion 63 to transition to the second state can be done in a variety of ways depending on the material used. Examples include exposing the material to the light of a specific wavelength range or exposing the material to body temperature.

When shaping the outside portion 63, the surgeon should use the outside portion 63 to form a protective layer over the edge of the plate 12 and an adjacent exposed portion of the bone. In this fashion, the cushion 60 prevents irritation by surrounding tissue contacting the bone-implant interface. To prevent irritation due to friction, both the center portion 62 and the edge portion 63 can be made of a lubricious material or impregnated with a lubricant such as lubricine or hyaluronic acid. To minimize palpable differences between the plate 12 covered with the implant cushion 60 and native soft tissue adjacent to the implant when felt through the skin, the material(s) used to form the center portion 62 and edge portion 63 may be visco-elastic. Materials used having a first and second state should be visco-elastic at least when the material is in its second state. As should be clear from the foregoing, the center portion 62 may be formed into a predetermined fixed shape prior to implantation of the cushion 60 and the second edge portion 63 is formed into a desired shape after implantation. This is important to provide an overall shape that provides suitable cushioning because the shape of the implants being cushioned are often modified and adjusted during implantation to accommodate the shape and location of the skeletal anatomy to which the implant is attached and achieve the desired medical benefit.

FIGS. 13-16 will now be referenced to describe a method of inserting a plate beneath the skin and muscle known as minimally invasive plate osteosynthesis (MIPO). MIPO may also be employed to fasten the cushion 60 to a plate. An advantage of MIPO is that large dissection and the associated disruption of healing potential is avoided.

Figures 13, 14:
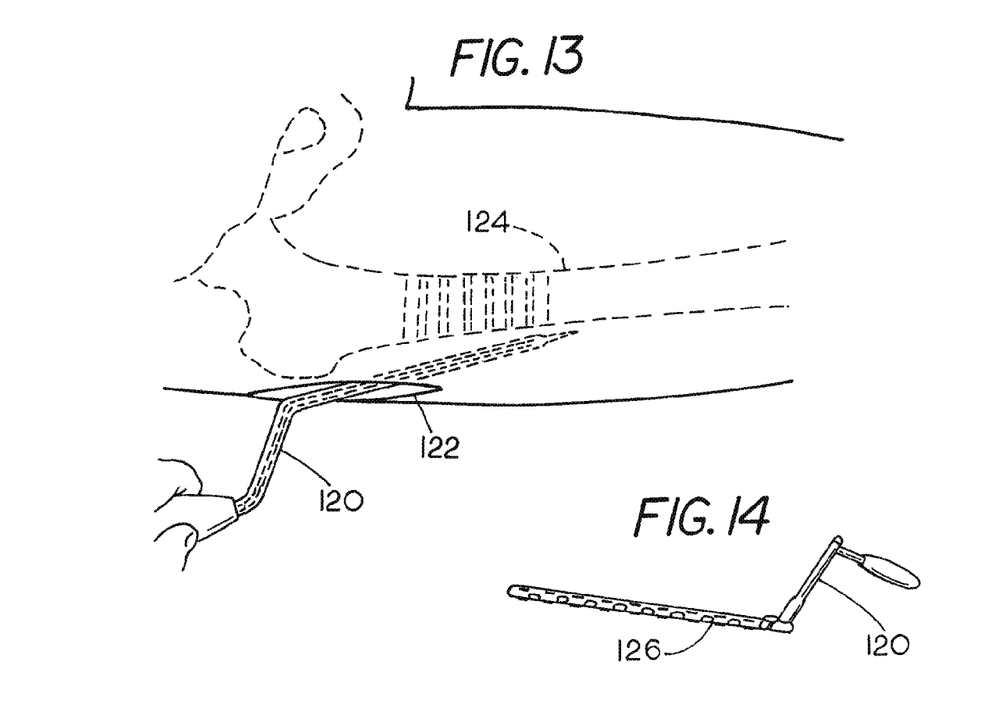
FIG. 13 is a view showing a tool being used to create a tunnel between a bone and surrounding soft tissue.
FIG. 14 shows a bone plate attached to the tool of FIG. 13.
Figures 15, 16:
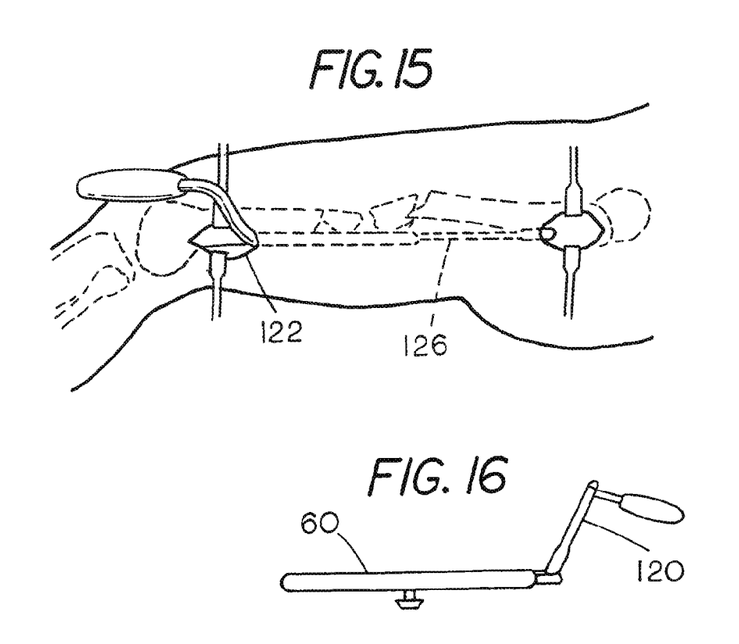
FIG. 15 shows the tool of FIG. 13 being used to position the bone plate within the tunnel.
FIG. 16 shows a cushion attached to the tool of FIG. 13.

When MIPO is performed, a long insertion tool, such as epiperiosteal elevator 120, is used to create a submuscular tunnel 122 adjacent a bone 124 to be treated as shown in FIG. 13. The plate 126 to be implanted can then be temporarily secured to the epiperiosteal elevator 120 as shown in FIG. 14 and introduced from either the proximal or distal end of the tunnel 122 depending on the nature of the fracture being treated and the preference of the surgeon. Using the epiperiosteal elevator 120, the plate 126 is positioned adjacent the bone at the desired location and fastened to the bone. The epiperiosteal elevator 120 is then detached from the plate 126 and retracted. When the cushion 60 is to be employed, the cushion 60 can then be attached to the epiperiosteal elevator 120 as shown in FIG. 16, introduced through either end of the tunnel and advanced through the tunnel to a position beneath the muscle and adjacent the top of the plate 126. The cushion 60 is then attached to the plate 126 as described above and detached from the epiperiosteal elevator 120 which is then retracted.

Those skilled in the art will recognize that various modifications and enhancements to the embodiments described above can be made without deviating from the invention. Likewise, alternative embodiments not described above incorporating the invention may be employed. Thus, the foregoing disclosure is not intended to be limiting. The scope of the invention is only limited by the claims which follow.

What is claimed is:

1. A kit comprising:
   a. at least one implantable medical device having an outer surface with a hole therein, the at least one implantable medical device selected from a group consisting of screws, plates, rods and formed augmentation structures;
   b. a medical implant cushion comprising a first portion and a second edge portion, the first portion having a predetermined fixed shape comprising a negative under surface corresponding to an outer surface of the implantable medical device, and having a button tab projecting from the negative under surface for insertion into the hole in the implantable medical device to attach the cushion to the implantable medical device, the second edge portion made of a biocompatible, non-absorbable polymer having a first state and a second state, wherein when the polymer is in the first state the polymer is formable into a desired shape adapted to cover at least a portion of the implantable medical device, and wherein the second state is a second final polymerization state in which the polymer retains the desired shape and is visco-elastic; and
   c. an insertion tool adapted to be temporarily attached to the cushion for positioning the cushion adjacent the implantable medical device so that the button tab is aligned with the hole in the outer surface of the implantable medical device upon implantation thereof.

2. The kit of claim 1 wherein the polymer is adapted to change from the first state to the second state by exposure to body temperature.

3. The kit of claim 1 wherein the polymer is adapted to change from the first state to the second state by exposure to light of predetermined concentrated wavelengths.

4. The kit of claim 1 wherein the polymer is impregnated with a lubricant.

5. The kit of claim 4 wherein the lubricant is lubricin.

6. The cushion kit of claim 4 wherein the lubricant is hyaluronic acid.

7. The kit of claim 1 further comprising preformed channels in the first portion of the cushion.

8. The kit of claim 1 wherein the cushion further includes an elongate radio-opaque marker.

9. The kit of claim 1 wherein the polymer is selected from a group consisting of polyurethanes, poly (dimethyl siloxane) derivatives, hyaluronan, polymer foams, and polymer hydrogels.

10. The kit of claim 1 wherein the implantable medical device is a screw having a screw head, said screw head having a contour.

11. The cushion of claim 10 wherein the negative undersurface of the cushion matches the contour of the screw head.

12. The kit of claim 1 wherein the implantable medical device is a plate adapted for placement relative to a bone inside a body, the plate comprising different portions having different contours and the desired shape configuration of the polymer has a molded negative inner surface matching the contours of at least one portion of the plate.

13. The kit of claim 12 wherein the second edge portion of the cushion is adapted to form a protective layer.

14. The kit of claim 1 wherein the implantable medical device comprises a plate having at least one edge and adapted to be attached to a bone by at least one screw having a screw head.

15. The kit of claim 14 wherein the desired shape of the polymer, at least when in the second state forms a protective layer.

16. The kit of claim 1 wherein the implantable medical device is a formed augmentation implant having a portion with contours.

17. The kit of claim 16 wherein the cushion comprises a molded inner surface matching the contours of the portion of the formed augmentation implant.

18. The kit of claim 1 wherein the implantable medical device comprises a rod adapted for fusing the spine and the cushion is adapted to cover at least a portion of the rod, the cushion having an increased thickness near a bottom end of the rod such that outside forces applied to the lower portion of the rod are spread by the cushion.

19. The kit of claim 1 wherein the implantable medical device has an outer edge and is adapted to be attached to a bone, and the cushion is adapted to cover at least a portion of the outer edge of the implantable medical device to provide a smooth tapered contour over said outer edge.

20. The kit of claim 1 wherein the cushion has a second hole for temporarily attaching the cushion to the insertion tool.

21. The kit of claim 1 wherein the cushion has at least one hole in its first portion for temporarily attaching the insertion tool to the cushion.

* * * * *